(12) United States Patent
Schmotzer

(10) Patent No.: US 6,325,829 B1
(45) Date of Patent: Dec. 4, 2001

(54) CUP FOR A KNEE-JOINT PROSTHESIS

(75) Inventor: Hans Schmotzer, Aarau (CH)

(73) Assignee: Plus Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/463,476

(22) PCT Filed: Jul. 20, 1998

(86) PCT No.: PCT/EP98/04520

§ 371 Date: Apr. 21, 2000

§ 102(e) Date: Apr. 21, 2000

(87) PCT Pub. No.: WO99/04732

PCT Pub. Date: Feb. 2, 1999

(30) Foreign Application Priority Data

Jul. 22, 1997 (DE) .............................................. 197 31 442

(51) Int. Cl.⁷ ...................................................... A61F 2/32
(52) U.S. Cl. ........................... 623/22.21; 623/22.23; 623/22.32; 623/23.53
(58) Field of Search ................ 623/22.11, 22.22, 623/22.23, 22.27, 22.32, 22.38

(56) References Cited

U.S. PATENT DOCUMENTS

| | | |
|---|---|---|
| 4,666,448 | 5/1987 | Ganz . |
| 4,892,549 | 1/1990 | Figgie, III et al. . |
| 5,370,704 | * 12/1994 | DeCarlo, Jr. .......................... 623/22 |
| 5,549,695 | 8/1996 | Spotorno et al. . |
| 5,782,928 | * 7/1998 | Ries et al. .............................. 623/22 |
| 5,972,032 | * 10/1999 | Lopez et al. ........................... 623/22 |

FOREIGN PATENT DOCUMENTS

| | | |
|---|---|---|
| 86 23 855.8 | 11/1986 | (DE) . |
| 40 21 677 | 1/1992 | (DE) . |
| 44 08 527 | 9/1995 | (DE) . |
| 0 380 055 | 1/1990 | (EP) . |
| 2 715 556 | 2/1994 | (FR) . |
| 2 159 416 | 3/1985 | (GB) . |
| WO 94/23670 | 10/1994 | (WO) . |
| WO 97/16138 | 5/1997 | (WO) . |
| WO 97/19656 | 6/1997 | (WO) . |

* cited by examiner

Primary Examiner—Corrine McDermott
Assistant Examiner—Urmi Chattopadhyay
(74) Attorney, Agent, or Firm—Knobbe, Martens, Olson & Bear, LLP

(57) ABSTRACT

Metal socket (10) for a joint endoprosthesis, the outer surface (11) of which comprises at least three circumferentially extending surfaces (12, 13, 14) of spherical segments each having a different radius (R1, R2, R3).

A metal socket for a joint endoprosthesis has an outer surface which includes at least three circumferentially extending, outwardly convex surface regions each having a different radius. The outwardly convex surface regions are exclusively surfaces of spherical segments, centers of which lie on a common axis of rotation, such that a radius of a medial spherical-segment surface is smaller than a radius of a polar spherical-segment surface, but larger than a radius of an equatorial spherical-segment surface.

7 Claims, 2 Drawing Sheets

CUP FOR A KNEE-JOINT PROSTHESIS

FIELD OF THE INVENTION

The invention relates to a metal socket for a joint endoprosthesis, which has the form of a bowl with a convex outer surface and concave inner surface. Such sockets are generally known and serve to support so-called inlays of polyethylene, ceramic or similar human-compatible material. A socket of this kind is often used as a component of an artificial hip joint. As a rule such sockets are made of titanium or a titanium alloy. When they are implanted without the use of cement, it is advantageous for the outer surface to be roughened or porous, in order to promote adhesion of the bone and growth of the bone into the pores of the socket.

The patent EP 0 380 055 B1 discloses a hemispherical socket that is flattened so as to depart from the circular or spherical shape in the region of its pole.

In the patent WO 94/23670 it is proposed that the outer surface of a hip-joint socket comprises an ellipsoidal region.

These two previously known constructions are intended to improve retention in the bone in comparison to a purely hemispherical shell. However, trials have shown that this goal is only inadequately achieved with a geometry according to EP 0 380 055 B1. The object of this known construction is therefore merely to increase slightly the separation of the polar surface from the surface of the natural socket seating into which it has been force-fitted, so that pressure exerted on the polar surface of the socket when the bone in the natural socket seating is placed under load will not push the socket out of position. This retraction of the polar surface is intended to reliably prevent contact between it and the bone even when the bone is heavily loaded. In this case, retention of the socket in the natural socket seating depends entirely on a force-fitting in the equatorial region of the socket. Very often, however, this is insufficient. It is in acknowledgement of this problem that the proposal to make the outer surface of a hip-joint socket ellipsoidal is made in WO 94/23670. One result is that the polar surface is separated further from the bone, with the advantages described above; another is that the surface over which the socket is force-fitted into the natural seating is increased. However, a disadvantage is that it is more expensive to construct an ellipsoidal surface, because the manufacturing technology for such a three-dimensional shape is complex.

SUMMARY OF THE INVENTION

The object of the present invention is thus to create a socket of the kind cited above that, firstly, is characterized by an improved force-fitting within the natural socket seating and, secondly, is considerably simpler to manufacture than the construction according to WO 94/23670.

This object is achieved in accordance with the invention by configuring the outer surface of the socket such that it is specified by at least three spherical-segment surfaces, each with a different radius. Surfaces of spherical segments are considerably simpler to construct than an ellipsoidal surface, because of their rotational symmetry. With regard to its anchoring properties, the construction in accordance with the invention provides about the same advantages as the construction with ellipsoidal surface regions.

The greater the number of spherical-segment surfaces that define the outer surface of the socket, the less abrupt are the transitions between adjacent areas of the socket surface, with the consequence that stress peaks in the bone caused by such transitions are correspondingly reduced. Because these stress peaks have a detrimental effect on the stability with which the socket is anchored in the bone, it is important that they (and hence abrupt surface transitions) are avoided. This is achieved in accordance with the invention.

Advantageous structural details of the invention are described. In one embodiment, the centers of the spherical-segment surfaces lie on a common axis of rotation.

In order to flatten the socket in the polar region, the center of the spherical segment that forms the peripheral or equatorial surface is closer to the pole of the socket than the center of the spherical segment forming the surface near the pole, in particular closer than that forming the polar surface itself.

In order to fix the socket in the natural socket seating so that it does not rotate, it can be advantageous to provide the equatorial spherical-segment surface with ribs or similar elevations that are directed towards the pole.

It is also conceivable to replace the equatorial spherical-segment surface by a peripheral conical surface with a cone angle between 3 and 6 degrees. This embodiment is mainly advantageous when the natural socket seating must be specially shaped in the peripheral region. Then all that is needed is to mill-cut a complementary conical seating surface in this region.

It is also conceivable for the pole of the socket to be additionally flattened by forming a surface that extends perpendicular to the axis of rotation.

Finally, it is further conceivable for the axes of rotation of the individual spherical-segment surfaces to be displaced from one another in a direction perpendicular to the surfaces, so as to extend the socket or outer surface thereof in this direction. This embodiment is particularly suitable for revision sockets.

In principle it is also conceivable for the axes of rotation of the individual spherical-segment surfaces to be tilted with respect to one another. In all cases, however, the crucial consideration is that the outer surface of the socket is defined by at least three spherical-segment surfaces of differing radius.

BRIEF DESCRIPTION OF THE DRAWINGS

In the following an embodiment of a hip-joint socket in accordance with the invention is explained in detail with reference to the attached drawings, wherein.

DETAILED DESCRIPTION OF CERTAIN EMBODIMENTS OF THE INVENTION

Figure 1:
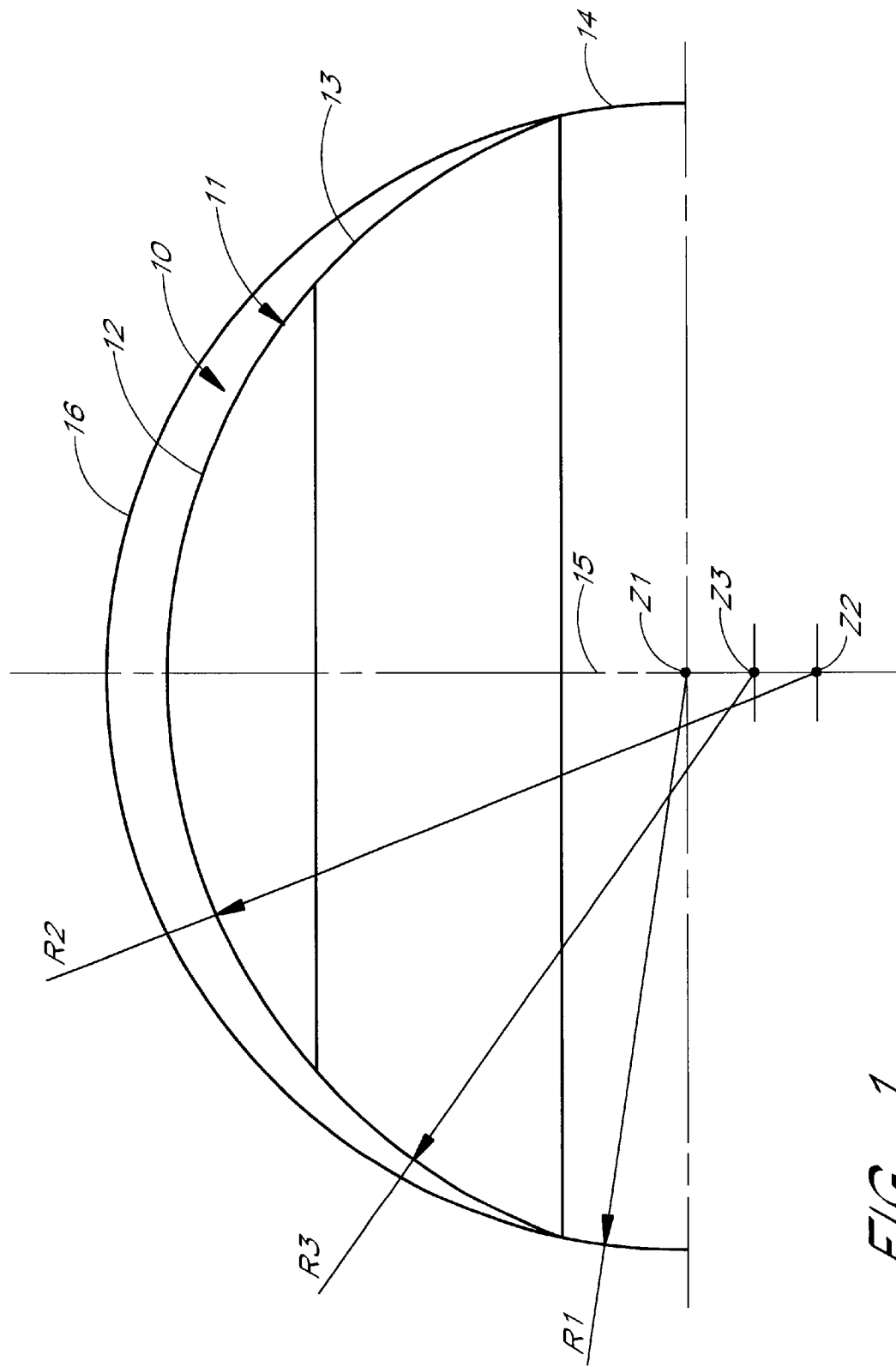
FIG. 1 shows a so-called triple-radius socket in side view, in which the various spherical-segment regions are shown in relation to a hemispherical shell in side view.

FIG. 1 shows a socket 10 with a convex outer surface 11 the shape of which is defined by three spherical-segment surfaces 12, 13, 14 that extend circumferentially, each having a different radius. The three spherical-segment surfaces 12, 13, 14 have a common axis of rotation 15. The centers Z1, Z2 and Z3 of the respective spherical-segment surfaces 14, 12 and 13 lie on this axis of rotation 15; of the corresponding radii R1, R2 and R3, the radius R3 of the medial spherical-segment surface 13 is smaller than the radius R2 of the polar spherical-segment surface 12 but larger than the radius R1 of the equatorial spherical-segment surface 14. As a result of this configuration and the choice of sphere radii, the surface in the region of the pole of the socket 10 is flatter than that of a purely hemispherical shell, which is represented in FIG. 1 by the semicircular arc 16.

As can further be seen in FIG. 1, in the embodiment shown there the equatorial spherical-segment surface 14 and the polar spherical-segment surface 12 are each less wide than the interposed medial spherical-segment surface 13. Specifically, the equatorial and polar spherical-segment surfaces are each about half as wide as the medial spherical-segment surface 13. This embodiment ensures a better fit of the socket 10 into the natural socket seating. Hence the growth of the bone onto the socket is promoted, with the consequence that the socket becomes progressively more firmly seated.

Figure 2:
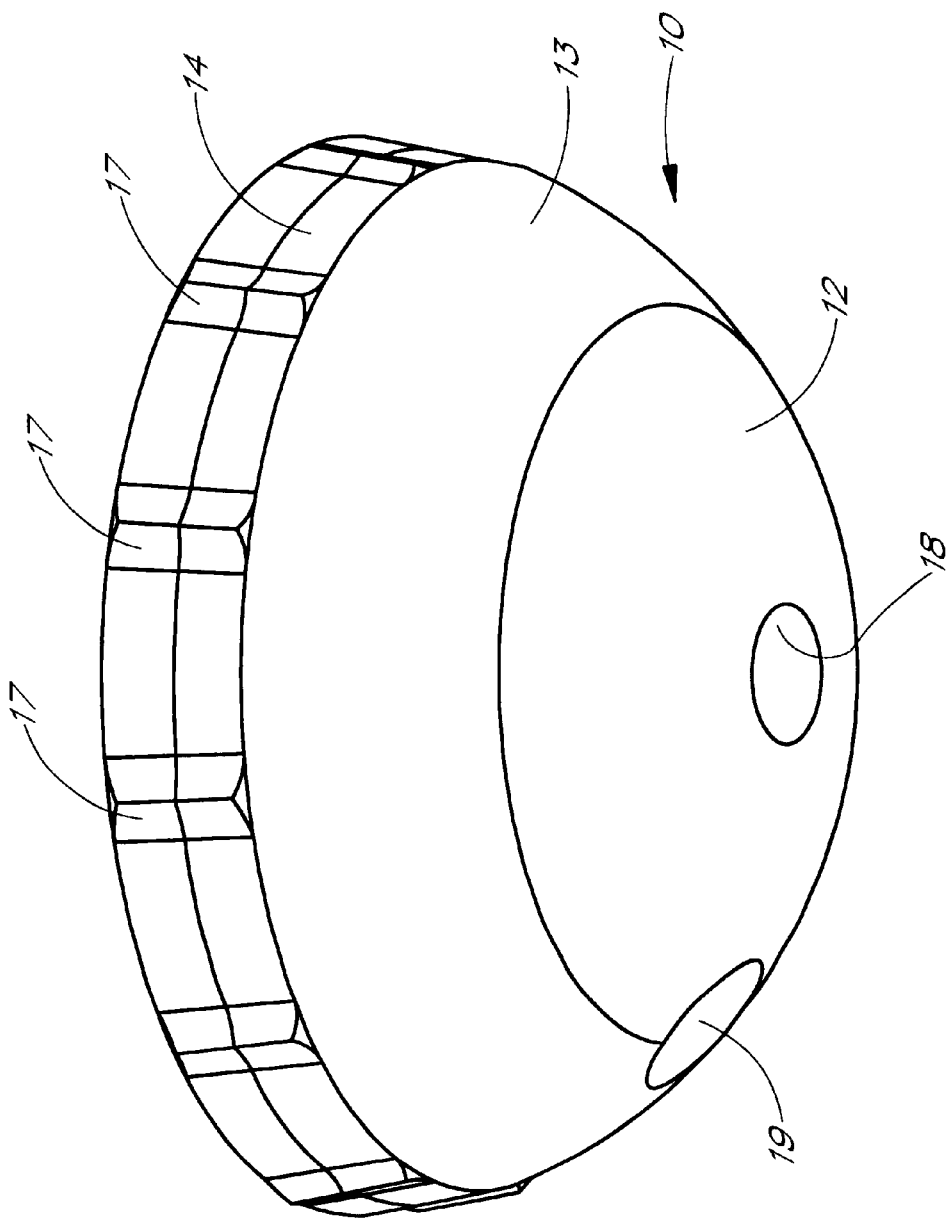
FIG. 2 shows a concrete embodiment of a triple-radius socket according to FIG. 1 in perspective as viewed at an angle from below and outside.

The socket according to FIG. 2 is additionally characterized by the presence on the equatorial spherical-segment surface 14 of ribs 17 directed towards the pole. The ribs 17 are uniformly distributed over the circumference and increase the rotational stability of the socket in the natural socket seating. Furthermore, they also contribute to increasing the firmness of the force-fitting in the natural socket seating.

It is conceivable to replace the equatorial spherical-segment surface 14 by a peripheral conical surface. This, too, can then be provided with ribs or similar elevations directed towards the pole.

The pole of the socket 10 can be made even flatter, e.g. by providing a surface that extends perpendicular to the axis of rotation 15. In the embodiment according to FIG. 2 a bore 18 that passes through the socket wall is provided at the pole to receive a bone screw. In the transition region between the polar and medial spherical-segment surfaces an additional bore 19 is formed. Where required, two bores 19 to receive bone screws can also be provided, at a predetermined angular distance from one another. The bores 18, 19 can also take the form of elongated holes, so that it is possible to select a suitable site for the bone screw within the limits set by the holes. This applies in particular to the openings disposed in the medial region. When these are formed as elongated holes, they preferably extend in a longitudinal direction. At this juncture it should also be noted that it is in principle possible to replace the equatorial spherical-segment surface 14 by a peripheral cylindrical surface.

All the characteristics disclosed in the application documents are claimed as essential to the invention insofar as they are new to the state of the art, singly or in combination.

LIST OF REFERENCE NUMERALS

10 Socket
11 Outer surface
12 Surface of spherical segment
13 Surface of spherical segment
14 Surface of spherical segment
15 Axis of rotation
16 Semicircular arc
17 Rib
18 Bore through socket wall
19 Bore through socket wall

What is claimed is:

1. A metal socket for a joint endoprosthesis, an outer surface of which comprises at least three circumferentially extending, outwardly convex surface regions each having a different radius, wherein the outwardly convex surface regions are exclusively surfaces of spherical segments, centers of which lie on a common axis of rotation, such that a radius of a medial spherical-segment surface is smaller than a radius of a polar spherical-segment surface, but larger than a radius of an equatorial spherical-segment surface.

2. The socket according to claim 1, wherein the center of the equatorial spherical-segment surface lies closer to a pole of the socket than the center of the polar spherical-segment surface.

3. The socket according to claim 1, wherein the equatorial spherical-segment surface comprises ribs directed towards a pole.

4. The socket according to claim 2, wherein the equatorial spherical-segment surface comprises ribs directed towards a pole.

5. The socket according to claim 2, wherein the equatorial and polar spherical-segment surfaces are each less wide than the interposed medial spherical-segment surface.

6. The socket according to claim 1, wherein the equatorial and polar spherical-segment surfaces are each less wide than the interposed medial spherical-segment surface.

7. The socket according to claim 1, wherein the equatorial and polar spherical-segment surfaces are approximately half as wide as the interposed medial spherical-segment surface.

* * * * *